United States Patent [19]

Baucom

[11] 4,241,223
[45] Dec. 23, 1980

[54] F-PHENYLALKYLENE OXIDE DIACETYLENES

[75] Inventor: Keith B. Baucom, Gainesville, Fla.

[73] Assignee: The United States of America as represented by the Secretary of the Air Force, Washington, D.C.

[21] Appl. No.: 70,473

[22] Filed: Aug. 28, 1979

[51] Int. Cl.$^3$ ............................................. C07C 43/166
[52] U.S. Cl. .................................... 568/611; 568/660; 568/8; 568/13; 250/544 Y; 260/343.5; 562/596; 526/247; 526/285; 528/354; 528/392; 528/401
[58] Field of Search ................................. 568/611, 660

[56] References Cited

U.S. PATENT DOCUMENTS 3,661,967   5/1972   Anderson et al. ............... 568/660 X Primary Examiner—Bernard Helfin
Attorney, Agent, or Firm—Donald J. Singer; Cedric H. Kuhn

[57] ABSTRACT

F-phenylalkylene oxide acetylenes having the formula $C_6F_5C\equiv C(CF_2OCF_2)_nC\equiv CC_6F_5$, where n ranges from 3 to 8, inclusive. The diacetylenes are useful as monomers for preparing fluorinated polyether elastomers.

3 Claims, No Drawings

F-PHENYLALKYLENE OXIDE DIACETYLENES

RIGHTS OF THE GOVERNMENT

The invention described herein may be manufactured and used by or for the Government of the United States for all governmental purposes without the payment of any royalty.

FIELD OF THE INVENTION

This invention relates to F-phenylalkylene oxide acetylenes. In one aspect it relates to a process for synthesizing the acetylenes.

BACKGROUND OF THE INVENTION

A need exists for monomers for use in the preparation of polymeric materials that will fulfill requirements for dynamic seal applications, e.g., O-rings, gaskets, diaphragms, and the like, as well as sealant applications, e.g., fuel tank sealants, coatings, and the like. Such polymers should have good thermal, oxidative, and chemical stability as well as excellent low temperature properties. Elastomers based upon perfluorinated polyethers have been considered to be likely candidates for achieving the desired goal. However, up to the present time, it appears that only low molecular weight perfluorinated polyethers with little elastomeric character have been prepared. No widely accepted theoretical polymerization scheme is known that would lead to pure perfluorinated polyether elastomers. The present day approach to this problem is to prepare perfluorinated polyether prepolymers which can be used to prepare curable high molecular weight polymers. It is essential that the connecting group between the polyether segments have the thermal, oxidative and chemical properties demanded of the basic elastomer. The ideal basic polymer would be composed of $-CF_2CF_2O-$ repeating units connected by benzene rings.

It is an object of this invention to provide F-phenylalkylene oxide diacetylene monomers for use in the preparation of perfluorinated polyether polymers.

Another object of the invention is to provide a process for synthesizing the monomers.

Other objects and advantages of the invention will become apparent to those skilled in the art upon consideration of the accompanying disclosure.

SUMMARY OF THE INVENTION

The present invention resides in a F-phenylalkylene oxide diacetylene having the following formula:

$$C_6F_5C{\equiv}C(CF_2OCF_2)_nC{\equiv}CC_6F_5, \quad (I)$$

where n is an integer ranging from 3 to 8, inclusive.

In one embodiment, the present invention is concerned with a process for synthesizing the above-described acetylenes. The reactions involved in carrying out the process are shown by the following equations:

$$C_6F_5CH_2P(C_6H_5)_3Br \xrightarrow{BuLi} C_6F_5CH{=}P(C_6H_5)_3 \quad (A)$$
$$(II) \qquad \qquad \qquad (III)$$

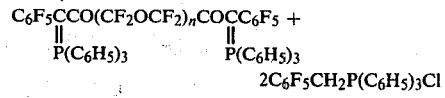

$$C_6F_5\underset{\underset{P(C_6H_5)_3}{\|}}{C}CO(CF_2OCF_2)_n\underset{\underset{P(C_6H_5)_3}{\|}}{C}OCC_6F_5 + 2C_6F_5CH_2P(C_6H_5)_3Cl \quad (C)$$

$$(V) \xrightarrow[\text{vacuum}]{\Delta} C_6F_5C{\equiv}C(CF_2OCF_2)_nC{\equiv}CC_6F_5 + 2(C_6H_5)_3PO .$$
$$(I) \qquad \qquad (VII)$$

As shown by equation (A), F-phenyl phosphonium salt (II) is converted to its ylid (III) using butyllithium. The butyllithium is mixed with compound (II), which is in solution in a suitable solvent, such as ethyl ether. Equimolar amounts of the compounds can be employed although it is often preferred to use about 5 to 15 percent excess of compound (II). The mixing is usually conducted in an inert atmosphere at about room temperature for a period of about 0.5 to 3 hours. Examples of inert gases that can be used include nitrogen, argon and helium.

Upon completion of the above-described reaction, compound (III) is reacted in an inert atmosphere with acid chloride (IV) (Equation B). In a preferred procedure, the acid chloride is merely added to the solution of compound (III) which is obtained as described in the preceding paragraph. The reaction temperature is generally about room temperature while the reaction time ranges from about 0.5 to 2 hours. The mole ratio of acid chloride to compound (III) is about 1:4.

The keto-ylid (V) recovered as a solid product from the reaction described in the preceding paragraph is pyrolyzed under a vacuum to give the diacetylene as shown by Equation (C). Heating of the keto-ylid is preferably conducted by gradually increasing the temperature from about 100° to 300° C. over a period of about 6 to 12 hours.

The F-phenyl phosphonium salt (II) is prepared from pentafluorobenzyl bromide as shown by the following equation:

$$C_6F_5CH_2Br+(C_6H_5)_3P \rightarrow C_6F_5CH_2P(C_6H_5)_3Br. \quad (D)$$

The phosphonium salt is disclosed by R. Filler and E. W. Heffern in J. Org. Chem., 32, 3249 (1967).

The acid chloride (IV) is prepared by hydrolyzing its acid fluoride derivative to the acid and then converting the acid to the acid chloride. The reactions involved are shown by the following equations:

$$FCO(CF_2OCF_2)_nCOF \xrightarrow{H_2O} HOCO(CF_2OCF_2)_nCO_2H \quad (E)$$

$$HOCO(CF_2OCF_2)_nCO_2H \xrightarrow[\text{Catalyst}]{SOCL_2}_{Pyridine} ClCO(CF_2OCF_2)_nCOCl. \quad (F)$$

Details of the preparation of the diacid fluoride and the diacid chloride are set forth hereinafter in Examples I and II.

The diacetylenes of this invention are particularly useful as monomers for preparing polymers by Diels- Alder polymerization. As a comonomer any suitable bis-diene can be used, but it is preferred to utilize a bis-α-pyrone. A particularly desirable bis-α-pyrone is one having the following formula:

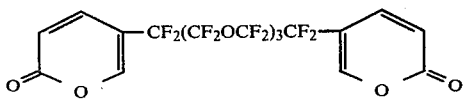

The bis-α-pyrone is prepared by coupling 5-bromo-2-pyrone with a diiodide as shown by the following equation:

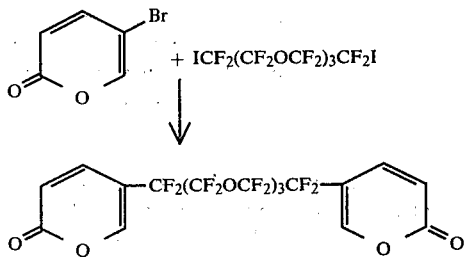

The 5-bromo-2-pyrone is prepared by the method of Pirkle and Dines, J. Org. Chem., 34 2239 (1969) while the diiodide can be prepared from a mixture of F-oxaglutaryl fluoride and its isomeric lactone by the general method of Evans et al., J. Org. Chem. 33, 1839 (1968). The polymers obtained are cured through the F-aromatics with a dialkoxide, e.g., a dipotassium salt of hexafluoroacetone bis-phenol.

A more complete understanding of the invention can be obtained by referring to the following illustrative examples which are not intended, however, to be unduly limitative of the invention.

EXAMPLE I

Preparation of $FCO(CF_2OCF_2)_nCOF$

A three-liter, Morton flask was equipped with a magnetic stirrer, stopper and two stopcock adapters, one of which led to a vacuum manifold equipped with nitrogen by-pass through a mercury dip tube. The flask was provided with a heating mantle and a pyrometer thermocouple which was placed between the flask bottom and the mantle. Cesium fluoride (4.0 g; 0.026 mole) was added to the flask and heated at 230° C. under full mechanical pump vacuum for 5 hours. The flask was allowed to cool under vacuum overnight. The next morning tetraglyme (50 g; dried over 4A molecular sieves) was added through one of the stopcock adapters with the system under vacuum. The system was brought to positive pressure with nitrogen and the stopcock adapter through which the glyme had been added was removed, cleaned and replaced. The stopper was replaced by a thermowell. A mixture of F-oxaglutaryl fluoride and its isomeric lactone (210 g; 1.0 mole) was added to the evacuated flask through one of the stopcock adapters. The pressure rose to 510 mm Hg. The mixture was stirred at room temperature for 2 hours. During this period, the cesium fluoride reacted to give a white mixture. The flask was immersed in Tecsol and cooled with dry ice to −20° C. Tetrafluoroethylene oxide (TFEO) was added slowly so that the temperature of the vapor above the solution did not rise above 0° C. but remained at about −5° C. The pressure of TFEO was gradually increased until it was at atmospheric pressure. The internal temperature was kept at −5° C. and the bath temperature was maintained at about −20° to −25° C. After all of the TFEO had been added, the system was opened to the atmosphere through the mercury dip tube and left overnight to come to room temperature. The outlet of the mercury dip tube vented into a hood. The next morning the bottom layer was transferred under vacuum through one of the stopcock adapters to a tared, one-liter distillation flask (903 g crude). The upper glyme layer was poured cautiously into vigorously stirred water (500 cc). A bottom layer formed and was isolated (49 g). The sum of acid and acid fluoride indicated that 6.4 moles (742 g) of TFEO had been added. The crude oligomeric mixture was analyzed by GLC on 15% PFOX which indicated the following composition.

| FCO $(CF_2OCF_2)_n$COF | | |
|---|---|---|
| n | Wt% | Grams |
| 6 | 22.33 | 200 |
| 7 | 46.82 | 420 |
| 8 | 13.94 | 125 |

Distillation was carried out, using a 15-plate Oldershaw column, with the following results:

| Fraction | b. range, °C. | mm Hg | Wt., g | GLC, Wt % | n |
|---|---|---|---|---|---|
| 1 | 42–84 | 7 | 36.9 | | |
| 2 | 84–88 | 7 | 3.3 | | |
| 3 | 88–90 | 7 | 190.5 | 90.4 | 6 |
| 4 | 53–66 | 0.4 | 19.7 | | |
| 5 | 66–66.5 | 0.4 | 383.0 | 93.7 | 7 |
| 6 | 66.5–78.5 | 0.4 | 12.8 | | |
| 7 | 78.5–81 | 0.4 | 136.5 | 95.6 | 8 |
| 8 | Residue | | 48.7 | | |
| | | | 831.4 | | |

Samples (3, 5 and 7) of the above acid fluorides where n=6, 7 and 8, respectively, were redistilled, using a 15-plate Oldershaw column, with the following results:

| Fraction | n | bp °C./mm Hg | Wt., g | GLC, Wt% |
|---|---|---|---|---|
| 3 | 6 | 88–90/7 | 190.5 | 90.4 |
| 3a | 6 | 112–114/30 | 154.2 | 96.4[1] |
| 3b | 6 | Residue | 29.0 | |
| 5 | 7 | 66–66.5/0.4 | 393.0 | 93.7 |
| 5a | 7 | 126.5–128/23 | 28.0 | 98.0 |
| 5b | 7 | 128–129/23.5 | 289.0 | 98.0 |
| 5c | 7 | 129/23.5 | 42.0 | 98.8 |
| 5d | 7 | Residue | 17.5 | |
| 7 | 8 | 78.5–81/0.4 | 136.5 | 95.6 |
| 7a | 8 | 141–144/20.5 | 9.5 | |
| 7b | 8 | 144/20.5 | 49.0 | 97.5[1] |
| 7c | 8 | 138.5–139/19.5 | 52.5 | 98.5[1] |
| 7d | 8 | Residue | 20.7 | |

[1]Analyzed as the methyl ester.

GLC analyses of the acid fluorides were performed on a 10 foot, 20% QF1 column at 150° C. at 20 cc/min carrier flow. Some of the samples gave irreproducible results symptomatic of decomposition. These samples were analyzed as the methyl ester on 15% PFOX programmed from 200°–250° C. at 16° C./min, using 28 cc/min carrier flow. NMR of all three acid fluorides confirmed the assigned structure.

EXAMPLE II

Preparation of ClCO(CF$_2$OCF$_2$)$_6$COCl

The acid fluoride FCO(CF$_2$OCF$_2$)$_6$COF (50 g; 63 mmoles), prepared as described in Example I, was hydrolyzed to the acid in a polyethylene beaker with 10 ml of water. The resulting acid (white powder) was dried at room temperature in vacuo. The acid was then converted to the acid chloride by heating at reflux for 8 hours under a dry nitrogen atmosphere with 100 ml of thionyl chloride and 1 ml of pyridine. The crude acid chloride was then distilled to give 43 g (82.9% of theoretical) of slightly cloudy acid chloride (bp 133° C./23 mm Hg). After pressure filtration, 41.5 g of clear acid chloride was obtained. The above structure of the product was confirmed by infrared analysis.

EXAMPLE III

Preparation of (C$_6$H$_5$)$_3$P=C(C$_6$F$_5$)CO(CF$_2$OCF$_2$)$_6$COC(C$_6$F$_5$)=P(C$_6$H$_5$)$_3$ (C$_6$H$_5$)$_3$PCH$_2$(C$_6$F$_5$)Br [115 g; 0.22 moles (10% excess)] was added under a nitrogen blanket to a 5-liter, 3-neck flask fitted with a mechanical stirrer and a water-cooled condenser vented through a −183° C. trap to a nitrogen by-pass. Ethyl ether (3 lbs) was pressured into the flask through a 3-inch pad of Al$_2$O$_3$, and the mixture was rapidly stirred as butyllithium (0.20 moles) was added from a dropping funnel. As the butyllithium was added, the phosphonium salt went almost completely into solution and the solution became dark brown in color. After continued stirring for an additional half hour, acid chloride, ClCO(CF$_2$OCF$_2$)$_6$COCl, (41.5 g; 0.05 mole) was added dropwise from an addition funnel. As the acid chloride was added, large amounts of solids came out of solution. The mixture was then stirred for an additional half hour and a sample was removed for infrared analysis. The IR showed the keto-ylid having the above structure and no acid chloride.

An attempt was made to separate the solid phosphonium salt from the ether solution by pressure filtration, but rapid plugging of the filtering aid made separation almost impossible. Addition of water (1500 ml) resulted in two layers, a bottom aqueous layer containing the dispersed phosphonium salt and an upper ether layer. (The phosphonium salt was sparingly soluble in water.) The ether layer was separated, dried (MgSO$_4$), filtered, and concentrated to give 40 g (49% of theoretical) of tan-solid keto-ylid.

EXAMPLE IV

Preparation of C$_6$F$_5$C≡C(CF$_2$OCF$_2$)$_6$C≡CC$_6$F$_5$

The keto-ylid (19.2 g; 11 mmoles), prepared as described in Example III, was added to a 50 ml, single-neck flask fitted with a heated sidearm leading to a cooled receiver fitted with a vacuum take-off. The keto-ylid was then heated with stirring in vacuo (1–5μ) as follows:
150° C.—2 hours
185° C.—2 hours
185°–250° C.—4 hours.

Heating was then discontinued and, after cooling to room temperature, the receiver was found to contain a large amount of solids and a small amount of liquid. The sidearm was also found to contain a large amount of solids. The contents of the receiver and sidearm were washed with hexane, the hexane solution was passed through a column of basic alumina and concentrated to give 2.64 g (22.2% of theoretical) of diacetylene product. Infrared analysis confirmed that the product had the above structure.

As seen from the foregoing, the present invention provides F-phenylalkylene oxide diacetylenes which are useful as monomers in the preparation of perfluorinated polyether polymers. Because of the structure of the diacetylenes and the bis-α-pyrones used as comonomers therewith, the polymers are composed of —CF$_2$CF$_2$O— recurring units connected by benzene rings. Thus, the polymers are characterized by having the thermal, oxidative and chemical stability required of elastomeric materials to be used in dynamic seal and sealant applications.

As will be apparent to those skilled in the art, modifications of the present invention can be made in view of the foregoing disclosure without departing from the spirit and scope of the invention.

I claim:

1. A F-phenylalkylene oxide diacetylene having the following formula:

wherein n is an integer ranging from 3 to 8, inclusive.

2. The F-phenylalkylene oxide diacetylene according to claim 1 in which n is equal to 6.

3. A process for preparing a F-phenylalkylene oxide diacetylene which comprises the following steps:
(a) reacting an equimolar mixture of butyllithium and a F-phenyl phosphonium salt having the formula C$_6$F$_5$CH$_2$P(C$_6$H$_5$)Br within an inert atmosphere at about room temperature for a period of about 0.5 to 3 hours to obtain a product having the formula C$_6$F$_5$CH=P(C$_6$H$_5$)$_3$;
(b) reacting the product obtained in step (a) with acid chloride ClCO(CF$_2$OCF$_2$)$_n$COCl (in which n is an integer ranging from 3 to 8 inclusive) in a 4 to 1 mole ratio within an inert atmosphere at about room temperature for about 0.5 to 2 hours to obtain a keto-ylid having the formula:

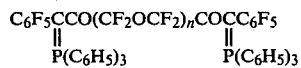

(in which n is an integer from 3 to 8 inclusive); and
(c) having the keto-ylid under a vacuum, at a temperature ranging from about 100° to 300° C. for a period of about 6 to 12 hours, thereby obtaining a F-phenylalkylene oxide diacetylene having the formula C$_6$F$_5$C≡C(CF$_2$OCF$_2$)$_n$C≡CC$_6$F$_5$ (in which n is an integer from 3 to 8 inclusive).